United States Patent
Tovey (10) Patent No.: US 8,922,858 B2
(45) Date of Patent: Dec. 30, 2014

(54) MOTION AXIS CONTROL AND METHOD FOR BIOSENSOR SCANNING

(71) Applicant: Cameron John Tovey, Painted Post, NY (US)

(72) Inventor: Cameron John Tovey, Painted Post, NY (US)

(73) Assignee: Corning Incorporated, Corning, NY (US)

(*) Notice: Subject to any disclaimer, the term of this patent is extended or adjusted under 35 U.S.C. 154(b) by 156 days.

(21) Appl. No.: 13/753,879

(22) Filed: Jan. 30, 2013

(65) Prior Publication Data

US 2013/0194647 A1    Aug. 1, 2013

Related U.S. Application Data

(60) Provisional application No. 61/592,901, filed on Jan. 31, 2012.

(51) Int. Cl.
*G02B 26/12*    (2006.01)
*G02B 26/10*    (2006.01)
*G01N 21/25*    (2006.01)
*G01N 21/77*    (2006.01)

(52) U.S. Cl.
CPC ............ *G02B 26/101* (2013.01); *G01N 21/253* (2013.01); *G01N 21/7743* (2013.01)

USPC ................. 359/197.1; 359/201.1; 359/201.2; 359/202.1; 359/202.2

(58) Field of Classification Search
USPC ....................... 359/197.1, 201.1, 201.2, 202.1
See application file for complete search history.

(56) References Cited

U.S. PATENT DOCUMENTS

| | | | |
|---|---|---|---|
| 6,586,257 B1 * | 7/2003 | Vuong | 436/165 |
| 2003/0092075 A1 * | 5/2003 | Pepper | 435/7.9 |
| 2010/0231907 A1 * | 9/2010 | Pien et al. | 356/326 |

* cited by examiner

*Primary Examiner* — Scott J Sugarman
*Assistant Examiner* — Mustak Choudhury
(74) *Attorney, Agent, or Firm* — John L. Haack

(57) ABSTRACT

A motion control system and a method for biosensor scanning which scans a light beam spot over one or more of the biosensors supported by a microplate with an optical scanner system, the method including:

defining a scan path for an optical scanner including selecting axes representing properties of the scan path and selecting a time series, calculating a piecewise polynomial function of time between each point in the time series; and scanning the light beam spot over one or more biosensors according to the defined scan path, as described herein.

15 Claims, 9 Drawing Sheets

MOTION AXIS CONTROL AND METHOD FOR BIOSENSOR SCANNING

CROSS-REFERENCE TO RELATED APPLICATIONS

This application claims the benefit of priority under 35 U.S.C. §119 of U.S. Provisional Application No. 61/592,901, filed Jan. 31, 2012, the contect of which is relied upon and incorporated herein by reference in its entirety.

This application is related to commonly owned and assigned U.S. Provisional Patent Application Ser. Nos. 61/534,604, filed Sep. 14, 2011, entitled "Motion Control System and Method For Biosensor Scanning," and 61/445,266, filed Feb. 22, 2011, entitled "Optical Reader Systems and Methods for Microplate Position Detection," but does not claim priority thereto.

The entire disclosure of any publication or patent document mentioned herein is incorporated by reference.

FIELD

The present disclosure relates to biosensor scanning such as performed in label-independent optical reader systems, and in particular to motion control systems and methods for biosensor scanning.

BACKGROUND

Manufacturers of optical reader systems seek new and improved optical reader systems that can be used to interrogate, for example, a resonant waveguide grating biosensor to determine if a biomolecular binding event (e.g., binding of a drug to a protein; stimulus induced changes in live cells) occurred on a surface of the biosensor. Of interest are improved scanning systems and methods having reduced vibrations and resonances, and having generally improved quality and efficiency of the biosensor readings obtained from the biosensor scanning.

SUMMARY

Disclosed are a system for motion axis control and a method for biosensor scanning with the system. The system includes a multi-axis (e.g., 2 to 8 axes) controller which specifies a sequence of moves for light beam scanning of a microplate having waveguide biosensors. An algorithm specifies movements, position, velocity, acceleration, ultra smooth motion, and like aspects. Attributes of the disclosed system and method include: that it permits, for example, the use of inexpensive (lowest cost) electronic configurations and mechanical components; the ability to do "jumps" between gratings during the scan routine; and a reduction in the cycle time needed to read a microplate, such as cycle time reductions of about half or 50% compared to existing methods and systems.

In embodiments, the present disclosure provides biosensor scanning systems and methods that can, for example, reduce scan system vibrations and resonances, and that can generally improve the quality and efficiency of the biosensor readings obtained from the biosensor scan.

In embodiments, the present disclosure provides a system and method for motion axis control in biosensor scanning, such as performed in label-independent detection (LID) optical reader systems, and in particular to the design of a multi-axis controller for scanning devices used in biosensor scanning.

BRIEF DESCRIPTION OF THE DRAWINGS

A more complete understanding of the present disclosure may be had by reference to the following detailed description when taken in conjunction with the accompanying drawings, where.

DETAILED DESCRIPTION

Reference is now made to embodiments of the disclosure, exemplary embodiments of which are illustrated in the accompanying drawings. The claims are incorporated into and constitute part of the Detailed Description.

The aforementioned Patent Application Ser. No. 61/534,604, the disclosure of which is incorporated herein by reference in its entirety, disclosed a method for adapting a conventional, general-purpose multi-axis motion controller to produce the desired scan paths. The prior disclosed method included control of the nominal beam scan path in the X-Y plane, and control of the parameters of superimposed oscillation properties such as amplitude, frequency, direction, and phase. The prior disclosed multi-axis motion controller was designed to produce motion that is smooth not only in value (position) but also in $1^{st}$ and higher order rates of change (e.g., velocity, acceleration, and like parameters). This is because the scanning mirror used in certain MEMS-SLID biosensor scanning platforms may have a high tendency to resonate if excited at certain frequencies. Discontinuities in motion, and parameters of oscillation are known to produce such frequencies. Discontinuities in rates of change can also produce such frequencies, but the effect lessens with the order in which the discontinuity occurs. Thus, a discontinuity in position has greater impact than in velocity, and a discontinuity in velocity has greater impact than acceleration, and so on.

Figure 1:
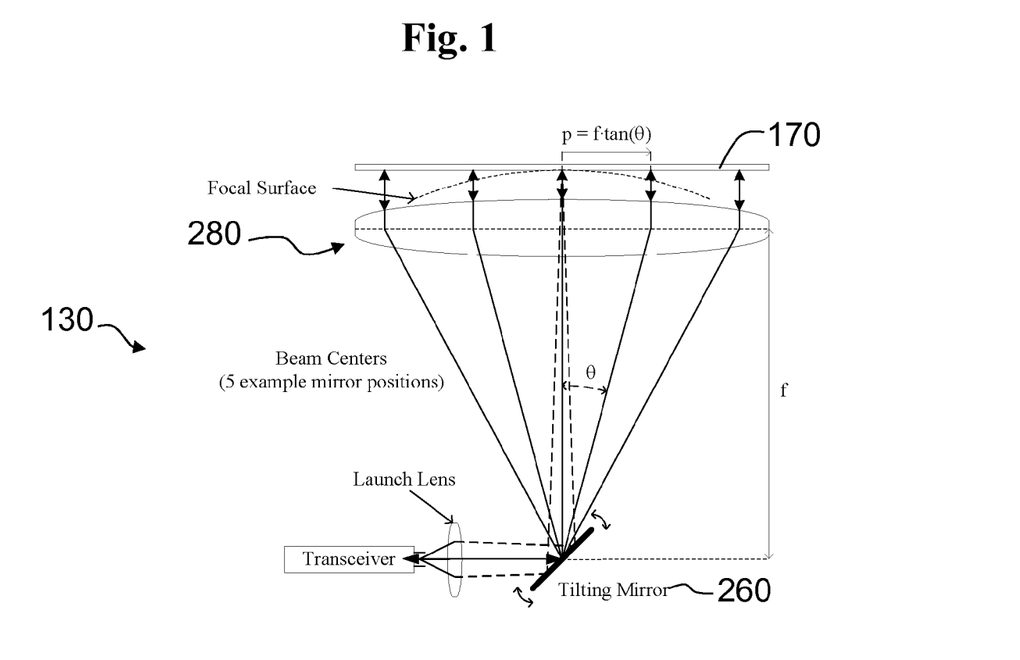
FIG. 1 is a schematic diagram of a prior scanning optical reader system.

Referring to the Figures, FIG. 1 schematically shows a MEMS-SLID reader used to interrogate a LID biosensor, for example, for drug discovery. The MEMS-SLID technology used in certain LID readers, was disclosed in WO 2011/017147 A1. This interrogation method scans an oscillating measurement beam over the biosensors on a plate. The use of oscillation is fundamental to reader operation, and is also used to calibrate the system using the methods contained in the aforementioned patent application No. 61/445,266. A light source inside a transceiver module produces a small spot of broad spectrum infrared (IR) light on the microplate. A two-dimensional mirror scans the spot over one or more of the sensors on the plate. A spectrometer in the transceiver module observes the reflection. In the scanning optical system 130, an objective lens 280 (i.e., an f-theta lens) is placed between microplate 170 and scanning mirror device 260, with the focal point of the objective lens located at the center of rotation of the mirror of scanning mirror device 260. Scanning optical system 130 exhibits tangential distortion, with the beam position on the sample being p=f·tan(θ), where f is the focal length of the f-theta objective lens 280.

Figure 2:
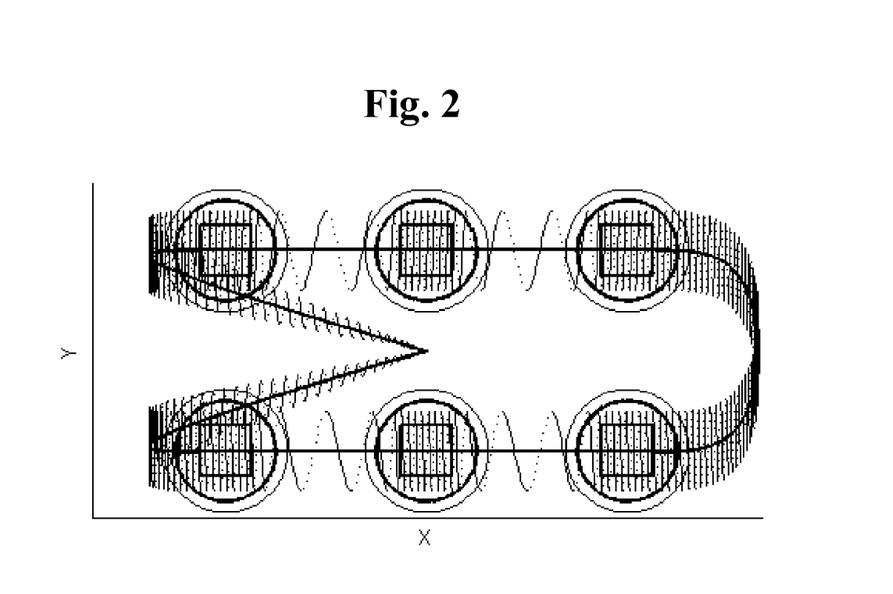
FIG. 2 shows an exemplary MEMS-SLID scan path used in the disclosed system and method.

FIG. 2 shows an exemplary MEMS-SLID scan path used in the disclosed inventive system and method for a sample having six wells. The scan path can begin in the center of the plate region (vertex), the move to the starting point of the first scan ("top left") to sequentially scan the top three wells (circles) having biosensors (squares) and having two rapid motions (or "jumps") in between adjacent wells. The scan path can then change direction (e.g., turns a "corner") to repeat the process in the reverse X direction before "leading out". In this example, the sinusoidal oscillation frequency is constant throughout. The baseline (center of oscillatory) motion is shown as a bold line in the center of the oscillation.

Figure 3:
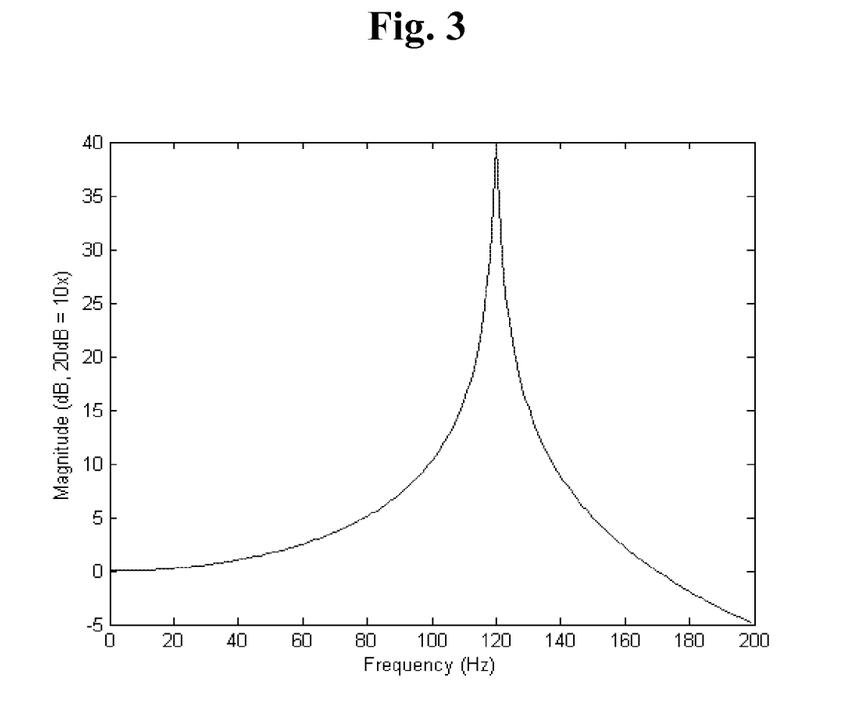
FIG. 3 shows an example frequency response of a MEMS mirror from a model.

FIG. 3 shows an example frequency response of a MEMS mirror from a model. In this instance, the resonant frequency is 120 Hz and the Q-factor (i.e., response level at resonance) is 100× the amplitude of the non-oscillatory response, which is equivalent to +40 dB (power).

Figure 4:
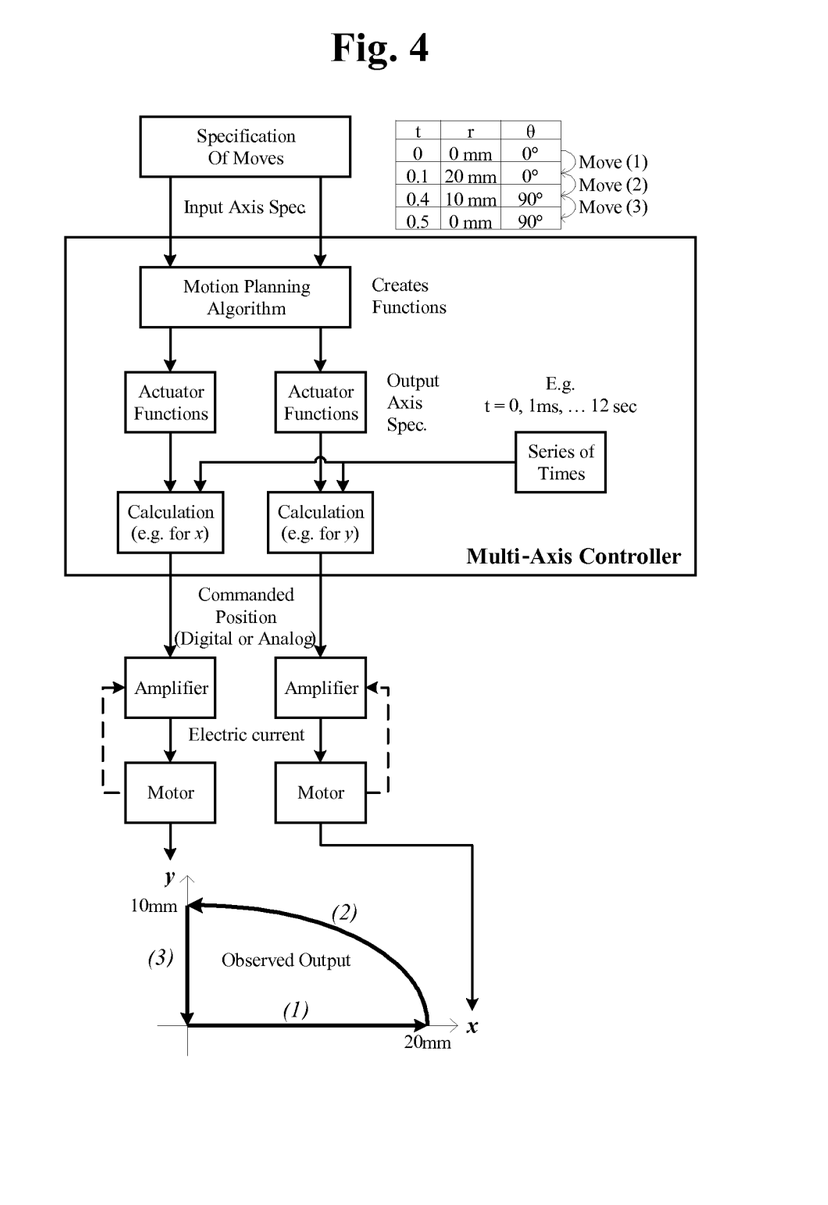
FIG. 4 shows an exemplary schematic of a general multi-axis controller.

FIG. 4 shows a schematic of a general multi-axis controller, shown here to illustrate a two-axis example. An example is shown in the embedded table where an application specifies motion "commands" or moves in polar coordinates (r, θ) between two consecutive points in time for selected times (t) and observes the motion on a Cartesian (X-Y) gantry.

Figure 5:
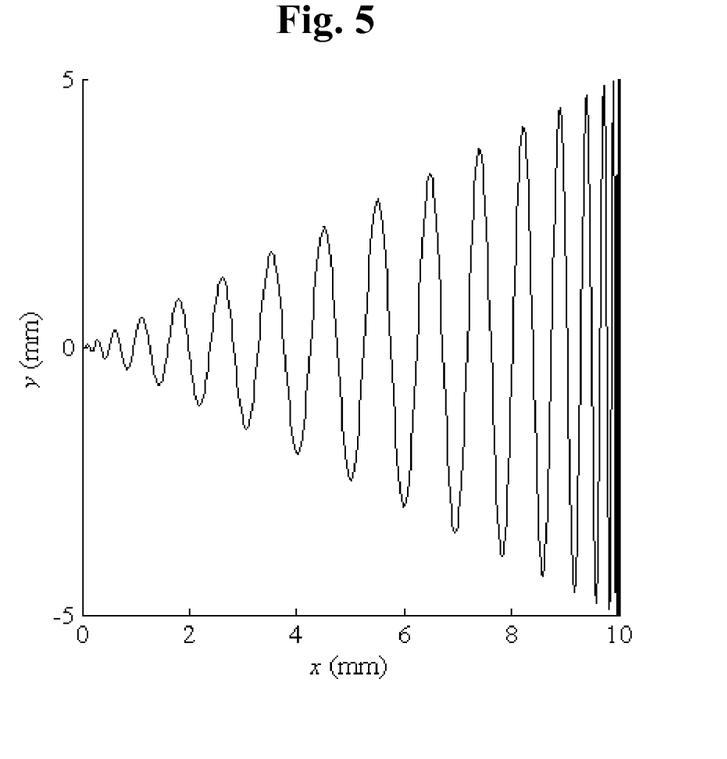
FIG. 5 shows a prior example which considered combining axis motion in non-linear ways.

FIG. 5 shows an example from the aforementioned Patent Application Ser. No. 61/534,604, which considered combining axis motion in non-linear ways, in particular, to control paths with oscillation in certain LID readers. In the present disclosure axes named "x0" and "y1" have been combined using x=x0(t) and y=y1(t)·sin(ωt).

The Texas Instruments TALP1000B MEMS mirror used in certain Corning MEMS-SLID systems has a resonant frequency in the range of 120 Hz and a resonant response over 100 times that of non-oscillatory situation. A typical response for this device is shown in FIG. 5. Many alternative devices that are capable of both tracing non-oscillatory curves with relatively rapid oscillation have low resonant frequencies (Q-points) and high resonant response (Q-factor) compared with "traditional" motion systems, such as industrial automation. Such devices necessarily have an extremely light load compared with the motion force (e.g., from the electromagnets). Galvanometers or related devices such as voice-coils are examples.

Figure 6A:
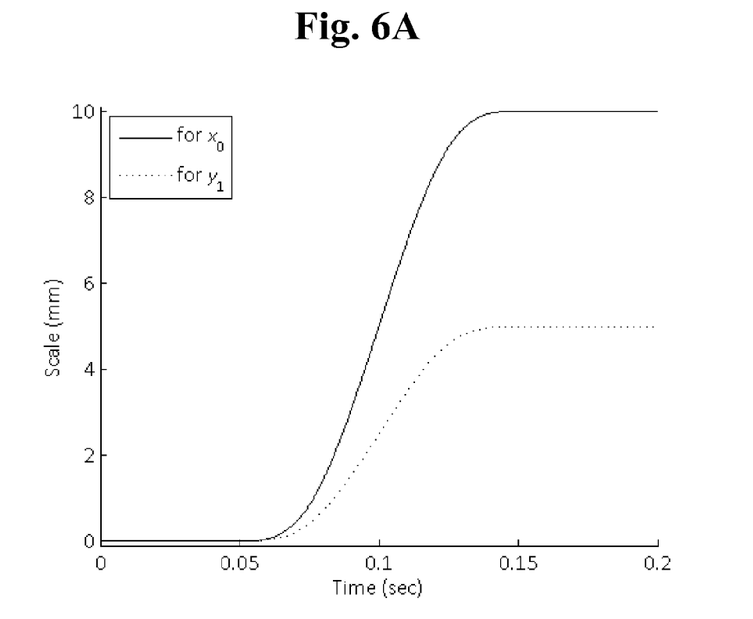
FIGS. 6A and 6B, respectively, show position (6A) and velocity (6A) for the axes shown in FIG. 5.
Figure 6B:
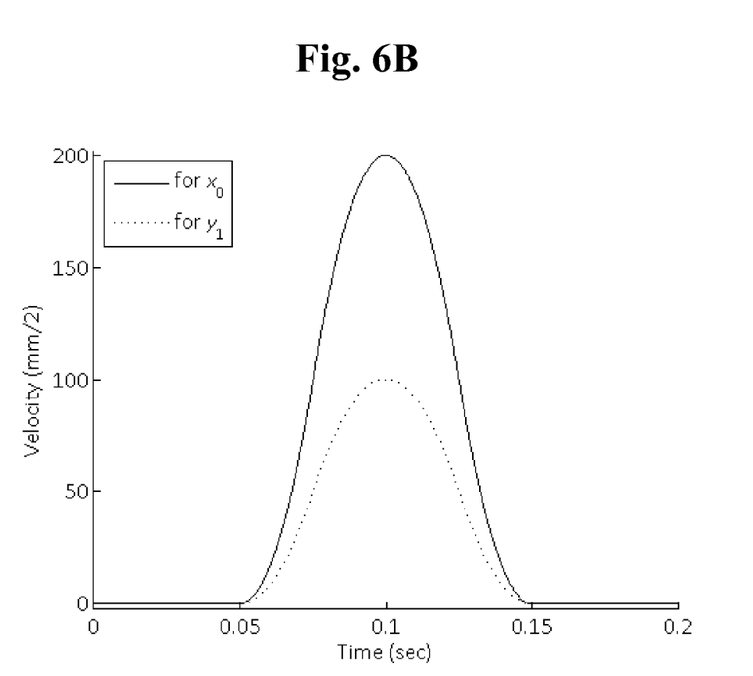

FIGS. 6A and 6B, respectively, show position (6A) and velocity (6A) for the axes shown in FIG. 5. The move starts at time 0.05 seconds and ends at 0.15 seconds.

Figure 7A:
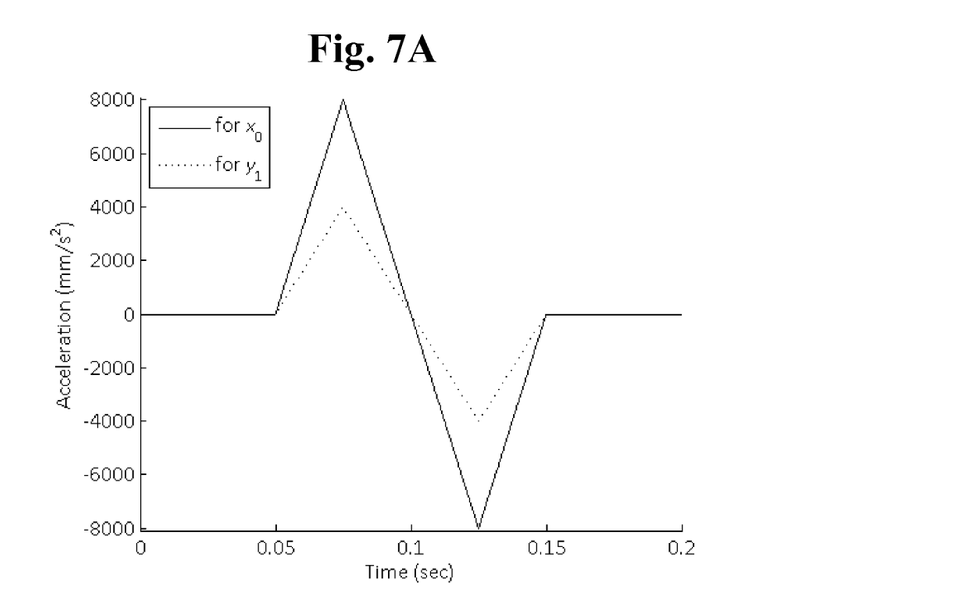
FIGS. 7A and 7B, respectively, show scan beam acceleration (7A) and Jerk (7B) plots for the axes shown in FIG. 5.
Figure 7B:
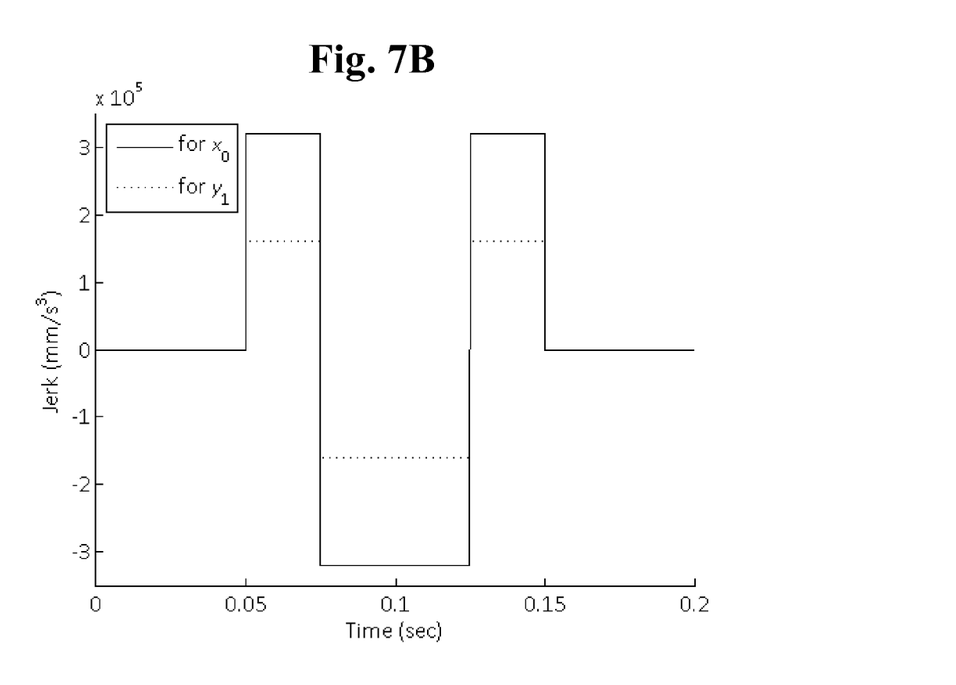

FIGS. 7A and 7B, respectively, show scan beam acceleration (7A) and Jerk (7B) plots for the axes shown in FIG. 5. The move starts at time 0.05 seconds and ends at 0.15 seconds. A 3-piece cubic form is evident from inspection of the plots.

Figure 8:
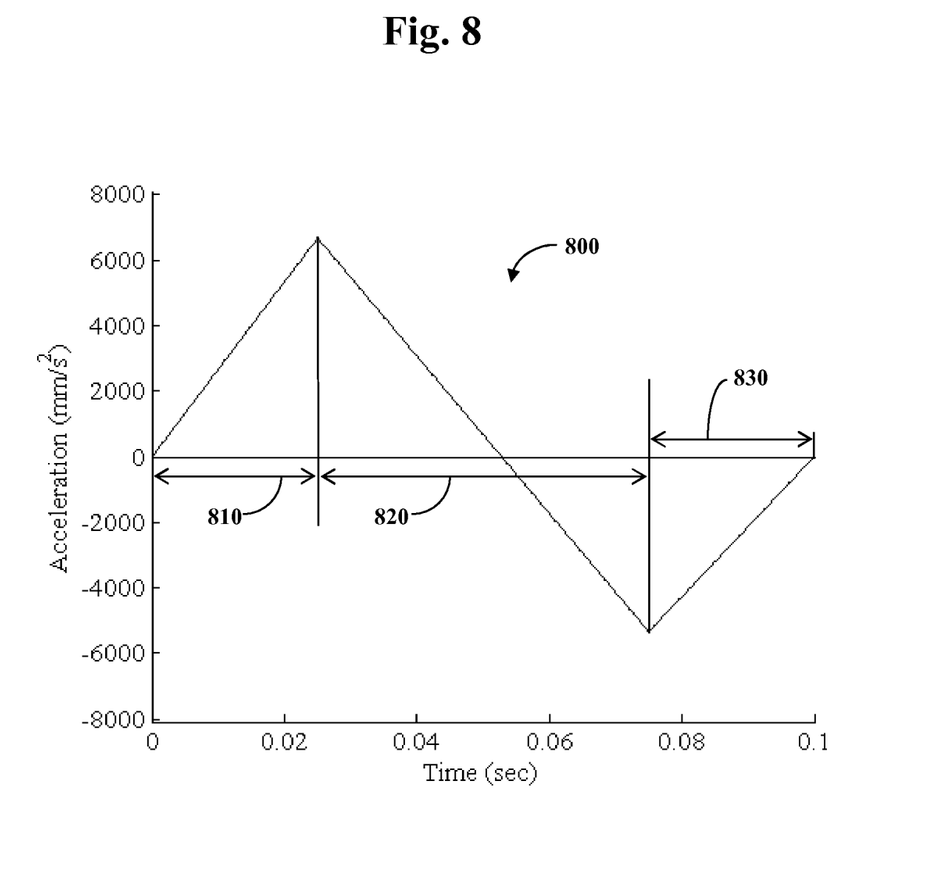
FIG. 8 shows an acceleration plot for an exemplary 3-piece cubic spline.

FIG. 8 shows an acceleration plot for an exemplary 3-piece cubic spline (800). Jerk is the slope of acceleration, in this instance consisting of three (3) piecewise constants whose time intervals are labeled Cubic 1 (810), 2 (820), and 3 (830).

Figure 9A:
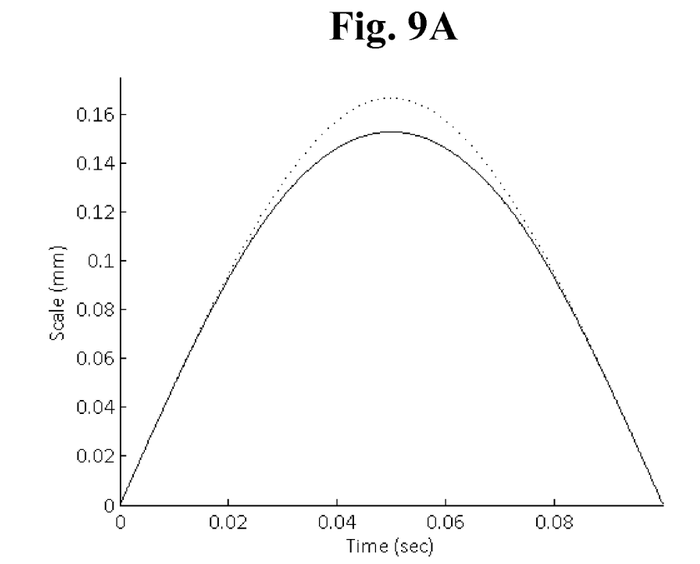
FIGS. 9A and 9B, respectively, show exemplary position (9A) and velocity (9B) for a MEMS-SLID "reverse" or retro-scan move.
Figure 9B:
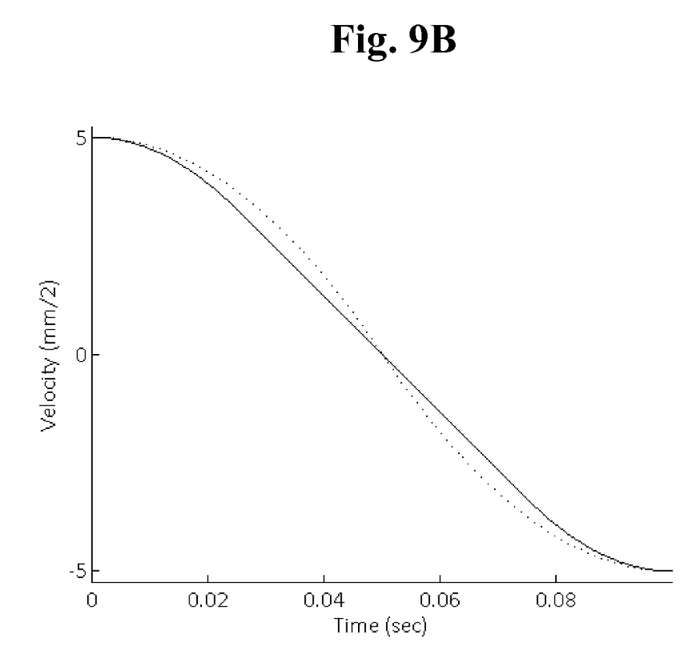

FIGS. 9A and 9B, respectively, show exemplary position (9A) and velocity (9B) for a MEMS-SLID "reverse" or retro-scan move. The start and end positions are the same, in this instance, arbitrarily shown as 0 mm. Velocity in the reverse direction retains its magnitude, and the initial and final acceleration are zero. The solid line is a 3-piece cubic spline that uses fixed timing apportioning ("Candidate 3F") and the dotted line is a 2-piece cubic spline using variable time apportioning ("Candidate 2F").

Figure 10A:
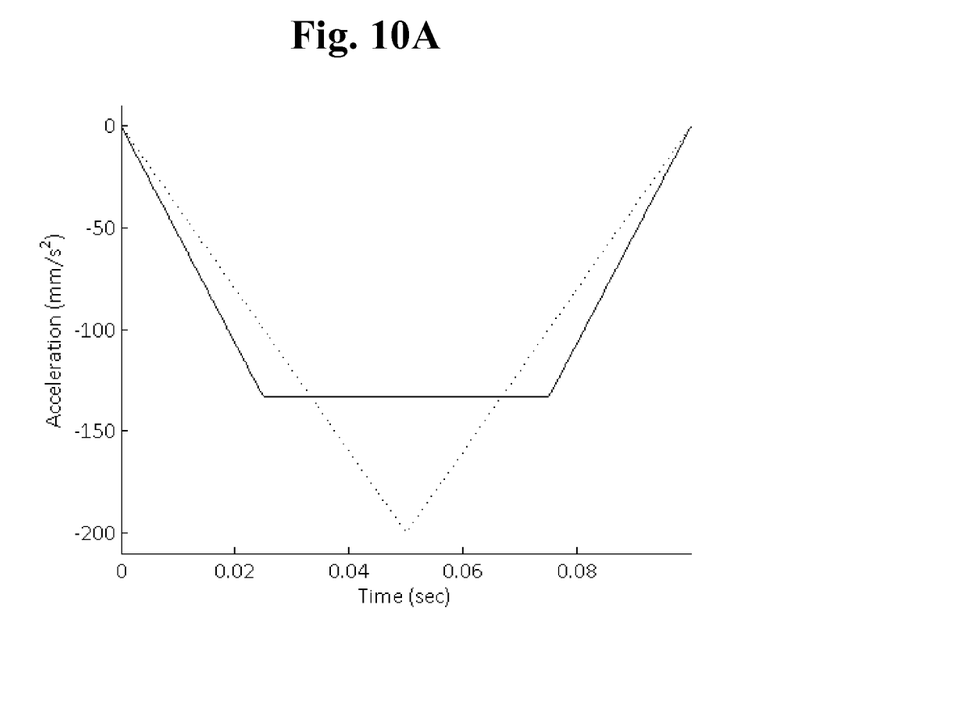
FIGS. 10A and 10B, respectively, show exemplary acceleration (10A) and Jerk (10B) curves for the MEMS-SLID "reverse" or retro-scan beam move shown in FIG. 9.
Figure 10B:
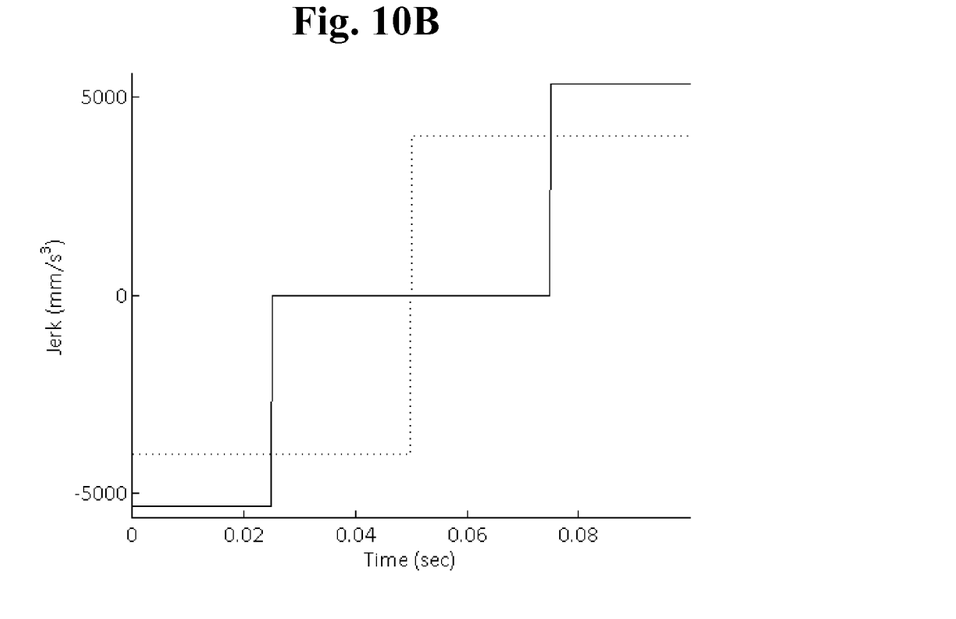

FIGS. 10A and 10B, respectively, show exemplary acceleration (10A) and Jerk (10B) curves for the MEMS-SLID "reverse" or retro-scan beam move shown in FIG. 9. The solid line is a 3-piece cubic spline using fixed timing apportioning ("Candidate 3F"), and the dotted line is a 2-piece cubic spline using variable time apportioning ("Candidate 2F"). Observe that the 2-piece cubic spline move minimizes absolute jerk magnitude, while the 3-piece cubic spline move has lower internal jerk discontinuity.

Algorithms for general purpose control are generally known (see for example, Nguyen, et. al., "On Algorithms for Planning S-curve Motion Profiles," *International Journal of Advanced Robotic Systems*, Vol. 5, No. 1, 2008, pp. 99-106.), although these algorithms can become complex if velocity and acceleration end points need to be controlled. If so, expensive state-of-the-art controllers may be necessary. Such functions are necessary in certain MEMS-SLID readers, for example, the scanning beam must move in a constant velocity mode to scan across wells, and move rapidly point-to-point between wells while starting and ending with the scan velocity to avoid a sudden jump in speed.

Analysis of the algorithms used in high end general purpose control revealed that most of the complexity originates from trying to meet position, velocity, and acceleration end-point criteria, under constraints on maximum velocity and acceleration, e.g., for reasons of safety legislation (especially in robotics) and device capability. By comparison, certain MEMS-SLID readers having a MEMS mirror, with its large available force and small mass are not practically constrained in this manner. The disclosed system and method use controller memory effectively, i.e., the present method purposely does not calculate and store every point for a scan path. The disclosed system and method improves operational performance by stripping unnecessary constraints from the control algorithm(s), and focuses instead on the minimization of resonance through smoothness in position, velocity, and acceleration. The disclosed system and method uses minimal computational and memory resources.

In embodiments, the system includes a multi-axis motion controller for controlling motion parameters of MEMS mirrors, or like devices. In embodiments, for each axis, the application (i.e., master control software) using the motion controller supplies:

a series of points in time;
a specified value of that axis at each point in time (e.g., position, oscillation amplitude);
a $1^{st}$ order rate of change of the value at each point in time (e.g., velocity, rate of change of amplitude); and
a $2^{nd}$ order rate of change of the value at each point in time (e.g., acceleration).

Multiple axes are coordinated and use time as a common variable. In embodiments, the series of points in time may be the same for all axes under consideration.

The controller is programmed to calculate a piecewise cubic function, referred to herein as a "plan," for each axis that meets all the specified conditions. This plan can be appended to any current plan, including the case where the current plan is in progress but has not been completed. The controller is programmed to evaluate the plan in successive increments of time. Axis value (e.g., position), and if required, velocity and acceleration are digitally output to post-processing steps such as control loops for position, velocity, or combinations thereof, to control oscillation.

A value oscillates when it repeats in a periodic manner. One dimensional motion containing oscillation can always be written as a value $x=x_0+x_1 \cdot Osc(2\pi \cdot f \cdot t+0)$ where t is time, $x_0$ is the center of oscillation (non-oscillitory motion), $x_1$, f, $\phi$ are, respectively the amplitude, frequency, and phase of oscillation, and Osc is a unit periodic function having period $2\pi$ and a peak-to-center amplitude of one. An example of a unit period function is the sine function.

In an example from the aforementioned Patent Application Ser. No. 61/534,604, any variables $x_0$, $x_1$, f, and $\phi$ may be separate axes under control, specified and computed using the previously mentioned plan. In a further example, if both axes of motion of a MEMS mirror can be controlled in this fashion, then $(x_0, y_0)$ is a two-dimensional center of oscillation, $(x_1, y_1)$ is a vector representing magnitude and direction of oscillation, and f and $\phi$ are respectively the frequency and phase of oscillation common to both dimensions. This calls for a six-axis motion controller capable of simultaneously evaluating and outputting six plans, which are coordinated with each other because each plan is specified in terms of time, which is common.

In embodiments, the disclosed system and method are advantaged in several respects including, for example:

Decreased move time: the system and method can perform fast moves between biosensors without causing significant vibration.

Increased repeatability: the system and method can reduce vibration, which can improve measurement repeatability or reproducibility.

The system and method can be readily implemented in new or existing scanning readers.

The system and method permit a relatively inexpensive motion control processor to be selected because of the realized reduction in memory, and reduction in real-time and non-real time processing.

In embodiments, the disclosure provides a method for scanning a light beam spot over one or more biosensors supported by a microplate with an optical scanner system having:
- a smoothness order n;
- a set of properties that describe the x and y position of the beam spot at any time;
- a series of points in time and at each point in time a value for each of the properties and the $1^{st}$ through the $(n-1)^{th}$ order rates of change of each of the properties;

the method comprising:
- defining an axis for each property used to describe the state of the beam spot;
- calculating for each axis an $n^{th}$ order piecewise polynomial function of time between each point in the series of points in time that equals the specified axis value and the $1^{st}$ through the $(n-1)^{th}$ order rates of change;
- producing a series of elapsed times between each point in the series of points in time;
- calculating each axis value from the polynomial function at each point in the series of elapsed times;
- calculating the x and y locations of the scan path from the axis values at each point in time; and
- sending the calculated x and y locations to the scanning optical system when each point in elapsed time series occurs to cause the scanning optical system to deflect the light beam and scan the beam spot over the defined scan path.

In embodiments, the additional points in time, together with the state of the beam spot at each additional point in time together with the $1^{st}$ through the $(n-1)^{th}$ order rates of change of the state of the beam spot can be appended to a scan path that is in progress.

In embodiments, the piecewise polynomial function can be, for example, a cubic spline.

In embodiments, the piecewise polynomial function can be, for example, of the $3^{rd}$ order and has 3-pieces.

In embodiments, the polynomial function is substantially continuous throughout in axis value and the $1^{st}$ through the $(n-1)^{th}$ order rates of change.

In embodiments of the method, between at least one pair of consecutive points in time at least one of the following applies:
- there are n polynomial pieces, and the duration of each of the polynomial pieces are fixed ratios of the total duration between the points in time;
- there are n polynomial pieces, where the highest order coefficient of the n polynomial pieces have substantially the same absolute value, and the duration of each polynomial piece is a calculated parameter; or
- the polynomial is of the $3^{rd}$ order, there are two polynomial pieces, and the $3^{rd}$ order coefficient and duration of each piece are calculated parameters.

The polynomial in between each pair of consecutive points in time can be, for example, calculated using a method that minimizes the maximum discontinuity in the $n^{th}$ order rate of change for a section of the scan path. In embodiments, the section of the scan path can include, for example, the entire scan path.

In embodiments, the defined axes can be combined mathematically to form x and y positions, for example, according to the methods used in aforementioned U.S. Patent Application 61/534,604.

The elapsed times can be, for example, representative of elapsed time in the real time, the elapsed times can have intervals that are substantially smaller than the smallest interval of the specified selected time series, and the properties can include, for example, at least one of: x position, y position, oscillation amplitude, oscillation direction, oscillation frequency, oscillation phase, and combinations thereof.

In embodiments, the disclosure provides a system for scanning a light beam spot over one or more biosensors supported by a microplate with an optical scanner system, comprising:
- a motion controller configured to:
  - receive a series of points in time, and at each point in time the value of each scan path property and the $1^{st}$ through the $(n-1)^{th}$ order rate of change of each of the properties;
  - calculate a series of elapsed points in time between each received point in time; and
  - calculate the x and y locations of the scan path at each point of elapsed points in time as defined for the above described method; and
- an optical scanner system configured to receive the x and y locations of the scan path at each elapsed point in time, and thereafter deflect the light beam to scan the beam spot over the scan path.

The elapsed times are representative of elapsed time in real time, the elapsed times have intervals that are substantially smaller than the smallest interval of the series of points in time, and the properties include at least one of: x position, y position, oscillation amplitude, oscillation direction, oscillation frequency, oscillation phase, and combinations thereof.

In embodiments, the system can further include first and second digital amplifiers operably connected to the controller and respectively configured to convert the x and y locations of the scan path to drive output positions x and y, and to amplify the drive output positions x and y.

The amplified drive output positions x and y can be, for example, respective x and y currents or voltages.

The scanning optical system can include, for example, one of a scanning galvanometer, a flexure-based scanning mirror, a micro-electro-mechanical system (MEMs) mirror, an oscillating plane mirror, a rotating multifaceted mirror, and a piezo-electric-driven mirror.

In embodiments, the system can further include, for example, a system controller operably connected to the motion controller and configured to input the series of points in time, and at each point in time the value of each scan path property and the $1^{st}$ through the $(n-1)^{th}$ order rate of change of each of the properties to the multi-axis controller.

EXAMPLE

FIG. 4 illustrates the operation of a simple, two-axis motion controller. In this example, an external software application ("application") controls axes in two-dimensional polar coordinates to a machine tool on a Cartesian gantry. The axes are magnitude r and angle θ. The application supplies:

a series of points in time;
the desired value of r and θ at each point in time;
a $1^{st}$ order rate of change of r and θ at each point in time; and
a $2^{nd}$ order rate of change of r and θ at each point in time.

A specific example of a specification used to generate a motion plate ("plan") can be:

(r,θ)=(0 mm, 0°) to (20 mm, 0°) in 0.1 seconds,
then to (10 mm, 90°) in 0.3 seconds,
then to (0 mm, 90°) in 0.1 seconds,
then stop.

Specification of rates of change as mentioned previously have been omitted from the example for clarity, and can be assumed to be zero in the example.

The motion controller calculates a plan for each axis. In the example, the plans are functions of time for both r and θ, and that meet the specifications supplied by the application. In an example, each plan can be the aforementioned cubic spline. The controller also generates a sequence (i.e., series) of times representative of elapsed time in the physical world. For each such point in time, the controller evaluates the motion plan for each axis to generate the current value of r and θ. These are converted to Cartesian coordinates using the standard equations $x=r.\cos(\theta)$ and $y=r.\cos(\theta)$.

Definitions

A "move" as used herein refers to the segment of a motion plan between two consecutive points in time specified by the application. The moves that may be desired for certain MEMS-SLID readers are exemplified in FIG. 2. All instances can have a zero starting and zero ending acceleration except for blended moves. The term "move" here also covers situations such as changing oscillation amplitude, phase, or frequency. There is no mathematical difference between a move in position and oscillation amplitude. The differentiation is only a linguistic attribute and convenience. The term "move" also includes changes of value, rate of change of value (velocity), and $2^{nd}$ order rate of change of value (acceleration). Where axes are coordinated by the specification of the axes at common points in time, a move includes the segments of the motion plan for all the axes. Therefore, a move may be between points in X-Y space, and may include changes in oscillation amplitude, direction, frequency, and phase.

"Scanning" a beam across a biosensor is move that may call for a difference in non-oscillatory position, constant velocity, and no changes in other parameters. As the scan may be angled slightly to match biosensor orientation, this can involve a change in both X and Y.

"Skipping" a beam between wells is a move that may call for a difference in position, the same start velocity and end velocity, and having rapid acceleration in between. For scanning, this can involve X and Y.

"Reversing" direction is a move that may need a change in direction, in velocity, and can have the same non-oscillatory start and end point. In the example of FIG. 2, reversing is shown in the X direction after the end of the first row scan of biosensors and the start of the second row scan of biosensors.

"Point-to-point" moves require a change in position, where the start and end velocity are zero. In the example of FIG. 2, reversing is shown in the Y direction after the end of the first row scan of biosensors and the start of the second row scan of biosensors. In the example of FIG. 2, and in some commercial embodiments of MEMS-SLID, changes in oscillation amplitude also fall into this category. A point-to-point move is a special instance of a "skip", where the start and the end velocities are zero.

"Ramps" are moves at the start and again at end of the scan, where the position changes and the velocity changes, such as either from zero to the scan speed, or from the scan speed back to zero. In MEMS-SLID readers, this can occur in the X and Y direction at the start and at the end of a scan. Note that the oscillation amplitude change can occur simultaneously and is categorized as a point-to-point move.

"Null": The value does not change, for example, the oscillation amplitude during a move. A further example is waiting in a quiescent state for further instruction, such as occurs between scans.

"Blend": When any move is aborted prior to completion, a blended move may be appended from the current position to the start of the next move. This might happen, for example, during a search where a feature has been found. Typically neither the initial and final position nor the initial and final velocity is equal. In addition, the initial acceleration is typically non-zero. The final acceleration is specified by the next move in the plan (as above) and typically will be zero.

Blended moves are not necessary to implement MEMS-SLID readers, but can be desirable in other systems. Blended moves are the only moves in MEMS-SLID with non-zero initial acceleration. All moves in the disclosed MEMS-SLID system have zero final acceleration.

Where there are n biosensors, in an array of c columns and r rows, the number of each type of move(s) in a standard measurement cycle are listed in Table 1. For a quadrant of a 384-well microplate, n=96, c=12, and r=8. Skips, scans, and reverses are the most significant moves. Again note that a point-to-point is a special instance of a skip.

TABLE 1

Standard measurement cycle listing.

| Type | X Center Position | Y Center Position | X & Y Oscillation Amplitude |
| --- | --- | --- | --- |
| Scans | n | n | — |
| Skips | r (c − 1) | r (c − 1) | — |
| Reverses | r − 1 | — | — |
| Point-to-Point | — | r + 1 | 2 |
| Ramps | 2 | — | — |
| Null | — | — | 2 n − 1 |
| Total | 2 n + 1 | 2 n + 1 | 2 n + 1 |

Overview of the Method

A main task of the motion controller of the disclosure is to determine a value, such as by calculation, and if called for a $1^{st}$ and a $2^{nd}$ order rate of change, at a sequence of successive times defined by a controller update rate. This collection or sequence of points forms the "motion path". The time interval between these calculated points can typically be many orders of magnitude less than that of the specific application.

In embodiments, in a certain Corning MEMS-SLID reader an update of each axis can be, for example, at up to 50 kHz. The MEMS-SLID application software specifies conditions at, at for example, up to 200 time points (199 moves) over 120 seconds, with intervals between time points varying, for example, from 0.01 to 5 seconds, from 0.02 to 4 seconds, from 0.03 to 3 seconds, from 0.04 to 2 seconds, including intermediate values and ranges. There can be, for example, 4- to 6-axes in that application, and values are stored as 32-bit numbers. Observe in this instance 137 Mbytes of memory may be called for to store all points for all axes for the scan path. For the largest interval between application specified points, 5.7 Mbytes can be necessary. The microprocessor selected for the design, one of the highest end processors in its class but still inexpensive at $17, has only 512 Kbytes of memory An overarching strategy of the disclosure is to specify the scan beam motion path as a table of functions for each axis. In an exemplary instance, a cubic spline type function can be selected. This function is a piecewise cubic having up to three pieces per axis for each move. The total memory required is 48 bytes per axis per move (4 coefficients, 32-bits each, 3 pieces), or 56 kbytes, for the 6-axes, 200 application-specified point path mentioned in the example above.

A cubic spline was selected because it can be made to meet all the necessary conditions while maintaining continuity in position, velocity, and acceleration. Cubic forms are a common form in industrial controllers because it is known that the $3^{rd}$ order derivative is related to machine tool wear and hence needs to be controlled. That justification is irrelevant in the present disclosure's applications. However, modeling and experimentation both showed that small discontinuities in the $3^{rd}$ order derivative had an acceptably small impact.

The disclosed method can be directly extended to higher orders. Higher orders work, and perform somewhat better than the $3^{rd}$ order solution, but the solutions do not always degenerate to readily apparent ("natural") solutions for some significant simple circumstances. One conclusion is that the direct generalization of this approach is not optimal beyond the $3^{rd}$ order.

Controller Function

FIG. 4 shows a schematic of the custom control system including a multi-axis controller embodying the disclosed method. The control system can include, for example:
- a microprocessor
- a memory for data;
- an application program;
- two digital-to-analog converters for output of the current position to two current drivers that drive the MEMS mirror; and
- four analog-to-digital converters for capturing position of the MEMS mirror.

In use the disclosed control system and method can perform one or more of the following functions or operations:
- contain the application software that generates and continually adds to the move sequence for each application axis;
- continually generates and appends function pieces describing motion to the path;
- continually generates a sequence of times representative of actual elapsed time;
- continually calculates the current value for each application axis;
- indexes through the functions the pieces in sequence as each expires;
- digitally filters the applications axis values;
- combines the application's axis values (e.g., $x_0$, $x_1$, $y_0$, $y_1$, f and θ) to generate physical axis set points (i.e., x and y), for example, using the method disclosed in aforementioned Patent Application Ser. No. 61/534,604;
- converts the physical axis set points into two currents that drive the MEMS mirror; and
- optionally closes a position loop by comparing the physical axis set points with mirror feedback.

Move Definition and Formulation

The strategy used in the disclosure is to calculate the section of the scan path for a single-axis move between two application specified time points in isolation. Continuity of the overall path in position, and in the $1^{st}$ and $2^{nd}$ order rates of change is guaranteed because the end time of one move is the start of time of the next move; every move then shares data with both the previous and next move. The application coordinates an arrangement of axes, if required, by specifying start and end points for the axes at the same time.

The following information is available for a single-axis move between two application specified time points:
- the start and end times, represented by the relative time difference T (see below);
- the start and end axis value, referred to as "position", $s_I$ and $s_F$; the start and end axis rate of change, referred to as "velocity", $v_I$ and $v_F$; and the start and end axis $2^{nd}$ order rate of change, referred to as "acceleration", $a_I$ and $a_F$.

In embodiments, each move (and therefore the overall path) is a piecewise $n^{th}$-order polynomial function that is globally continuous in up to the $(n-1)^{th}$ order rate of change (mathematically, the entire path is n−1 times continuously differentiable). A piecewise function with these properties is known in mathematics as a "spline". Where the application requires continuity in the $n^{th}$ order rate of change, the application specifies the start and end axis rates of change up to the $n^{th}$ order, and an $(n+1)^{th}$ order spline is called for. This disclosure primarily describes the cubic spline (i.e., $3^{rd}$ order) because a cubic is the lowest order polynomial capable of describing continuous acceleration (the $2^{nd}$ order rate of change above).

To simplify the equations, and without loss of generality, the method will also use "relative" time for each cubic piece. Relative time is defined to be zero at the start of any piece. Relative time is easily related to time as specified by the application, because the length of time for which each cubic piece is valid is included as part of the spline definition.

Each move can be constructed as a cubic spline with one to three pieces (within the overall cubic spline). The pieces are easy to identify in acceleration and jerk plots. FIG. 8 shows an example of acceleration for a 3-piece spline.

An example formulation for the $n^{th}$ cubic piece in a spline is provided in Equation 1.1, where the variable s is used for value or position. The $1^{st}$ to $3^{rd}$ order derivatives (of time), referred to respectively as velocity v, acceleration a, and jerk J are shown for convenience:

$$sn(t) = s_0 + v_0 \cdot t + \frac{1}{2}a_0 \cdot t^2 + \frac{1}{6}Jn \cdot t^3 \quad \text{Eq. 1.1}$$

$$vn(t) = v_0 + a_0 \cdot t + \frac{1}{2}Jn \cdot t^2 \quad t = 0 \ldots Tn \quad \text{Eq. 1.2}$$

$$an(t) = a_0 + Jn \cdot t \quad \text{Eq. 1.3}$$

$$Jn(t) = Jn \quad \text{Eq. 1.4}$$

The cubic form for Equation 1.1 is arbitrary, and as mentioned previously this method may be extended to higher orders. The $3^{rd}$ order time derivative is referred to herein as "jerk". The (kinematic) equation of motion was selected so that the coefficients s0, v0, a0, and Jn have the standard physical meanings of position, velocity, acceleration, and jerk respectively. Constants before coefficients (e.g., the ⅙ before $Jn \cdot t^3$) may be altered or omitted from this form to essentially express position, velocity, acceleration, and jerk on alternative scales.

The "n" following quantities s, v, a, J, and T denote the $n^{th}$ cubic piece for that move. Subsequently, this "n" is often written as an explicit number. The postscript "n" is used only for understanding and readability, and is omitted in cases where the quantity in question is not generally compared between different cubic pieces. For example, $s_0$ in Eq. 1.1 is technically $s_0n$ because $s_0$ is different for each cubic piece. The "0" subscript is used for the coefficients $s_0$, $v_0$, and $a_0$ because these coefficients represent initial conditions, for example $s(0)=s_0$. The "0" subscript is omitted from the jerk coefficient (Jn) because Jn is the constant value of jerk for all time in the range T to Tn, so Jn is more than just an initial condition. In addition, the "n" following Jn is included because this quantity is often compared between cubic pieces.

Construction of the Motion Algorithm

The following sections discuss the construction of motion algorithms. Example equations are provided to illustrate the algorithm.

The First Cubic (or Polynomial)

The initial values and rates of change supplied by the application, that is the previously mentioned $s_I$, $v_I$, and $a_I$ determine $s_0$, $v_0$, and $a_0$ in Eq. 1.1 to 1.4 for the first cubic in each move:

$$s1(t) = s_I + v_I \cdot t + \frac{1}{2}a_I \cdot t^2 + \frac{1}{6}J1 \cdot t^3 \quad t = 0 \ldots T1$$

Example having One-Piece Scan Moves

If a move is expressed with a single cubic piece, the completion time T1 is the application specified move time T. Only J1 is free for meeting the three remaining (end) conditions $s_F$, $v_F$, and $a_F$ and a general solution is not possible. There are degenerate conditions for which a solution is possible. One such example is a scan move where velocity is constant so jerk and acceleration are zero throughout the move, that is aI=aF=J1=0. The equation reduces to $s1(t)=s_I+v_I t$ and is only valid if $s_F \equiv s1(T)=s_I+v_I T$.

Solution Method for Unknown Time Allocation

Two exemplary methods (among others) are provided that can be used to construct closed form solutions to the problem of specifying a spline for moves. The two methods presented both assume the number of cubic pieces N is determined.

A first method applies when the validity times Tn for the polynomial pieces are not pre-determined.

Step 1: The application specified initial conditions (e.g., $s_I$, $v_I$, $a_I$) automatically set all the coefficients except the highest order coefficient (e.g., $s_0$, $v_0$, $a_0$) for the first polynomial (e.g., cubic) as mentioned previously. The highest order coefficient (J1 for a cubic) and T1 are to be determined.

Step 2: Use continuity between the last determined polynomial piece and the next piece in position and each rate of change to find the next set of coefficients ($s_0$, $v_0$, $a_0$) (for a cubic) in terms of the specified variables $s_I$, $v_I$, $a_I$ and previous to-be-determined variables Tn and (for a cubic) Jn. Repeat this step for each piece in succession. An example, for a second cubic piece is $s2_0=s1(T1)=s_I+v_I \cdot T1+½a_I \cdot T1^2+⅙J1 \cdot T1^3$ and so on for velocity and acceleration.

Step 3: For the last piece, substitute $$TN = T - \sum_{n=1}^{N-1} Tn$$

into Eqs. 1.1 to 1.3 and set these equal to the application specified final conditions. That is:

$$sN(TN)=s_F$$

$$vN(TN)=v_F$$

$$aN(TN)=a_F \quad \text{(Eqs. 3)}$$

The result of the first method are three simultaneous equations expressed in terms of the application defined initial and final axis values and rates of change (e.g., $s_I$, $v_I$, $a_I$, $s_F$, $v_F$, $a_F$), the move time T, the free higher-order coefficients (the Jn for cubic pieces), and the variables Tn for all but the last piece. Several solutions are discussed below.

Presentation of Solutions

Expressions for solutions can be very involved. The following sums and differences often simplify the expressions.

$$\Delta s \equiv s_F - s_I \quad \Sigma s \equiv s_I + s_F \quad \Delta v \equiv v_F - v_I \quad \Sigma v \equiv v_I + v_F \quad \Delta a \equiv a_F - a_I \quad \Sigma a \equiv a_I + a_F$$

Example with Two Pieces—Reverse Moves

Observe from the conclusion of the "Solution Method for Unknown Time Allocation" section for the $n^{th}$ order polynomial with N pieces there are n equations and 2N−1 unknowns. For a cubic spline (n=3) the number of equations equals the number of unknowns for N=2 (a two-piece cubic spline). There are some solutions, depending on the supplied values of initial and final velocity and acceleration.

To illustrate, consider the case where initial and final acceleration are zero as in MEMS-SLID (excepting for blended moves). The solution for T1 is given below.

$$T1 = \frac{\Delta v + 3 \cdot \Sigma v}{2 \cdot \Delta v} \cdot T - \frac{3 \cdot \Delta s}{\Delta v}$$

Observe this solution for T1 is not usually defined where $\Delta v=0$ (i.e., $v_F=v_I$). It turns out the only solution for $\Delta v=0$ is when the velocity is constant. In the solution, the second piece runs for no time (T2=0) and the solution degenerates to the one-piece case previously mentioned. Therefore, a two cubic piece spline cannot represent fast point-to-point moves, or skips between wells, and only represents scan moves by acting as a single cubic piece. From Table 1 these are the three most common moves in a MEMS-SLID system. In addition, in the case where $\Delta v \neq 0$, T1 or T2 can be negative (an example is where $s_I=s_F=v_F=0$, $v_I=1$) which is not realizable since time must always run in the positive direction. This demonstrates that a two piece cubic is not a general solution.

A two piece cubic can however represent a reverse in direction, and in that case is in a sense an optimal cubic form for minimizing jerk. The previous definition of a reverse move, started and ended at the same position ($s_I = s_F$) but velocities were opposite ($v_F = -v_I$). Initial and final acceleration were also required to be zero. The result is for T1 (from above) is given below with J1 and J2.

$$T1 = T2 = \frac{T}{2} \quad \bigg| \quad J1 = \frac{-8 \cdot v_I}{T_F^2} \quad \bigg| \quad J2 = -J1$$

This solution has optimal continuity in that it minimizes worst case discontinuity with the moves on either side. The only discontinuity in the cubic spline formulation of the disclosure is in jerk. Jerk is constant for every piece, but discontinuous at piece boundaries. In this particular instance, jerk for the two pieces is symmetrical about zero having equal magnitude, and opposite signs. This minimizes the absolute magnitude of jerk, which in turn minimizes the worst-case discontinuity at the boundaries with unknown up and down stream moves. The dotted lines in FIGS. 9A, 9B, 10A, and 10B, plot value, velocity, acceleration, and jerk, respectively, of an example reverse move, compared with an alternative method discussed further below. This two-piece move has the lower absolute jerk, although internal discontinuity is lower in the alternative.

A general solution for the two-piece move that does not require zero initial or final acceleration is given later in this disclosure. As above, the solutions are not valid in all instances since there are asymptotes and instances where T1 or T2 become negative. The reverse move above is a valid special example.

Example with Three Pieces—Skips Between Wells

In an n-piece $n^{th}$ order polynomial formulation with unknown time allocation for the pieces, there are n-equations (e.g., Eq. 3), n highest order coefficients, and n−1 times to be determined. There are n−1 degrees of freedom too many for a solution, since the number of independent equations must equal the number of independent variables for a solution. The three piece cubic formulation with unknown time allocation then has three equations (Eq. 3) and five variables to be determined: J1, J2, J3, T1, and T2. There are two degrees of freedom too many for a solution since two more constraints are needed.

As in the previous example, worst-case discontinuity in the highest order coefficient (in the cubic case, jerk) can be reduced by fixing the magnitude at a constant value. The sign of coefficient must then alternate for polynomials to be distinct. If consecutive polynomials ever have the same highest order coefficient, one is redundant. In the cubic example this means J2=−J1, and J3=J1. The unknowns are then J1, T1, and T2. No general solution was found to this problem with arbitrary initial and final acceleration.

Some solutions were found in the example having zero initial and final acceleration, and are presented later in the disclosure. For the example where $v_F = v_I$ and initial and final acceleration are zero, the solution is always valid. This is an important case because it includes skips and point-to-point moves. The notable finding is that time allocation is independent of the initial and final position and velocity; the result is:

$$T1 = \frac{T}{4} \quad \bigg| \quad T2 = \frac{T}{2} \quad \bigg| \quad T3 = \frac{T}{4}$$

For the general case where $v_F \neq v_I$ and the initial and final acceleration are not zero it is possible for T1 or T3 to be negative depending on the application specified conditions, and so a realizable solution is not always available.

Non-Optimal Moves

At this point, one necessary move has not been covered; namely ramps. While ramps are not numerous, they are required. It is also desirable to cover blended moves for further applications. There are also many situations having the initial and final conditions of position, velocity, and acceleration that do not exist in a basic MEMS-SLID scan but may find applicability in peripheral MEMS LID functions, such as in high-speed calibration algorithms, see for example, the above mentioned patent application No. 61/445,266.

The application requires a "fall back" solutions that, while not guaranteed to be optimal in minimizing jerk, produces continuous value (position), velocity, and acceleration, and definitely works. It is also desirable that these moves cover the example of non-zero initial acceleration to cover blended moves.

Solution Method for Fixed Time Allocation

Note again the three equation (Eq. 3) and the five variables to be determined: J1, J2, J3, T1, and T2. Instead of placing constraints on jerk for optimality, place constraints on time by defining each Tn as a pre-defined faction of the total time, that is:

$$Tn = \frac{T}{qn} \quad \bigg| \quad \sum_{n=1}^{N} qn = 1$$

The method follows that for unknown time allocation, except these equations are far simpler to formulate because there is only a single time variable (T), and it is the powers of time that make the solution complex. Formulation is a tedious but straightforward collection of coefficients of powers of T. The method is sufficiently similar to the unknown time allocation case that only the cubic case is presented here.

Step 1: The application specified variables $s_I$, $v_I$, $a_I$ automatically set $s_0$, $v_0$, $a_0$ for the first cubic. The term J1 remains a variable.

Step 2: Use continuity between the one cubic piece and next cubic piece to find the next $s_0$, $v_0$, $a_0$ in terms of the specified variables $s_I$, $v_I$, $a_I$ and the to-be-determined variables T and Jn. Repeat this step for each piece in succession. An example, for the second cubic is given by:

$$s2_0 = s1\left(\frac{T}{4}\right) = s_I + v_I \cdot \left(\frac{T}{4}\right) + \frac{1}{2} a_I \cdot \left(\frac{T}{4}\right)^2 + \frac{1}{6} J1 \cdot \left(\frac{T}{4}\right)^3$$

and so on for velocity and acceleration.

Step 3: For the last piece, form the three equations (Eqs. 6):

$sN(T/qN) = s_F$ $vN(T/qN) = v_F$ $aN(T/qN) = a_F$ (Eqs. 6)

This final result is three simultaneous equations (or n simultaneous equations for the $n^{th}$ order, n-piece case), expressed in terms of the application defined quantities $s_I$, $v_I$, $a_I$, $s_F$, $v_F$, $a_F$ and T, and the variables Jn for each cubic piece.

This formulation is not optimal in minimizing worst case jerk (jerk magnitude is not constant). However, there is always a closed solution for the $n^{th}$ order, n-piece case, including the 3-piece cubic case.

General Method Used in certain MEMS-SLID Readers

In embodiments, one sensible choice of time allocation is to use the values from the previous three piece cubic example that worked for "skip" and "point-to-point" moves. In the event that move is actually a skip or point-to-point move, the general solution will be the same as the already formulated skip move This means the previous skip solution need not be included in the final algorithm. Recall those time allotments were T/4, T/2, and T/4, respectively, so q1, q2, and q3 are respectively, 4, 2, and 4 in the formulation. This move will be most optimal when it represents the example under which the times allotment was calculated (i.e., skips or point-to-point).

In addition, this method applies to any fixed allotments of time found by solving Eq. 3 for any consideration of conditions, e.g., different ways of assigning jerk, or initial and final application conditions other than those considered here.

Comparison

Observe again FIGS. 9A and 9B, respectively, show exemplary position (9A) and velocity (9B) for a MEMS-SLID "reverse" or retro-scan move and plots of a reverse move. The two- and three-piece variable time methods both give the same solution. The three-piece version is degenerate. However, the three-piece fixed time method gives a different solution.

The three-piece method has lower internal jerk. This two-piece move has the lower absolute jerk which minimized jerk discontinuity at the start and down for arbitrary (i.e., unknown) upstream and down stream moves. However, in the MEMS-SLID example, it is known that the up and down stream "reverse" moves always scan across wells, where velocity is constant and jerk is zero. The three-piece method has the lowest jerk worst case discontinuity in the system (the largest is in the middle of the two-piece move). The discontinuity at the start of the scan (where it affects the process most) is lowest for the two-piece move. It is not apparent, which is the best choice.

A summary of the MEMS-SLID move types with the applicable methods is summarized in Table 2.

TABLE 2

| Method | "1" | "2T" | "3T" | "3F" | |
|---|---|---|---|---|---|
| Cubic Pieces | 1 Piece | 2 Piece | 3 Piece | 3 Piece | |
| Time Apportioning | — | Variable | Variable | Fixed | |
| Jerk Magnitude | — | Variable | Fixed | Variable | |
| Guaranteed Solution | | No | No | Yes | Best Method |
| Scans | Yes | Yes | Yes | Yes | All equivalent |
| Skips | — | — | Yes | Yes | 3T = 3F |
| Reverses | — | Yes | Yes | Yes | 2T = 3T or 3F |
| Point-to-Point | — | — | Yes | Yes | 3T = 3F |
| Ramps | — | — | — | Yes | 3F |

Algorithm in Full

The following procedure calculates a cubic spline between two application supplied points, where the time difference plus the initial and final position, the initial and final velocity, and the initial and final acceleration are given as: T, $s_I$, $s_F$, $v_I$, $v_F$, $a_I$, and $a_F$.

Preliminary

Calculate:

$$\Delta s = s_F - s_I \quad \Sigma s = s_I s_F \quad \Delta v = v_F - v_I \quad \Sigma v = v_I + v_F \quad \Delta a = a_F - a_I$$
$$\Sigma a = a_I + a_F$$

Perform the candidate identification, selection, and final calculation steps below.

Candidate 1: Single Piece

Examination of the following potential candidate is an optional part of the algorithm. Exclusion of this step will not reduce performance, but will consume more memory when these conditions are met.

Calculate:

$$T1 = T \quad \bigg| \quad J1 = \frac{\Delta a}{T} \quad \bigg| \quad s1(T) = s_I + v_I \cdot T + \frac{1}{2} a_I \cdot T^2 + \frac{1}{6} J1 \cdot T^3 \quad \bigg| \quad v1(T) = v0 + a0 \cdot T + \frac{1}{2} J \cdot T^2$$

If $$s1(T) = s_F \quad \text{and} \quad v1(T) = V_F$$

then the single cubic piece spline (N=1) defined by T1 and J1 is the best solution. Skip to the Final Form.

Candidate 2T: Two-Piece Variable Time Allotment

Examination of the following potential candidate is an optional part of the algorithm. However, not evaluating this candidate may reduce performance. This candidate is valid if the denominator (bottom line) of T1, J1, and J2 are all non-zero, and T1>0 and T2>0. Then the two-piece cubic spline (N=2) defined by T1, T2, J1, and J2 below is a candidate solution.

$$A = (\Delta a + \Sigma a) \cdot T^2 + (-2 \cdot \Delta v - 6 \cdot \Sigma v) \cdot T + 12 \cdot \Delta s$$

$$B = 2 \cdot T \cdot \Sigma a - 4 \cdot \Delta v$$

$$C = (\Delta a - \Sigma a) \cdot (\Delta a + 2 \cdot \Sigma a) \cdot T^2 + (8 \cdot \Delta v \cdot \Sigma a - 6 \cdot \Delta a \cdot \Sigma v - 2 \cdot \Delta a \cdot \Delta v) \cdot T + (12 \cdot \Delta a \cdot \Delta s - 8 \cdot \Delta v^2)$$

$$T1 = \frac{A}{B} \quad \bigg| \quad T2 = T - T1 \quad \bigg| \quad J1 = \frac{C}{A \cdot T} \quad \bigg| \quad J2 = \frac{C - B \cdot T \cdot \Delta a}{A \cdot T - B \cdot T^2}$$

Candidate 3T: Three Piece Variable Time Allotment

Examination of the following potential candidate is an optional part of the algorithm. However, not evaluating this candidate may reduce performance. This candidate calls for:

$$\boxed{a_I = 0 \mid a_F = 0 \mid \Delta v \neq C}$$

This candidate then is the below values T1≥0 and T3≥0. Then the three cubic piece (N=3) spline defined by T1, T2, T3, J1, J2, and J3 below is a candidate solution.

$$P = T^2 \cdot \Delta v^2 + 4 \cdot T^2 \cdot \Sigma v^2 - 16 \cdot T \cdot \Delta s \cdot \Sigma v + 16 \cdot \Delta s^2$$

$$T1 = \frac{T \cdot \Delta v - 4 \cdot \Delta s + 2 \cdot T \cdot \Sigma v + \sqrt{P}}{4 \cdot \Delta v} \mid T2 = \frac{T}{2} \mid T3 = \frac{T}{2} - T1$$

$$J1 = \frac{16 \cdot \Delta s - 8 \cdot T \cdot \Sigma v + 4 \cdot \sqrt{P}}{T^3} \mid J2 = -J1 \mid J3 = J1$$

Candidate 3F: Three Piece Fixed Time Allotment

Examination of the following candidate is required unless another candidate has been identified. This candidate always works (and is optimal if $\Delta v = \Delta a = 0$). It is defined by the three cubic piece (N=3) spline defined by T1, T2, T3, J1, J2, and J3.

$$T1 = \frac{T}{4} \mid T2 = \frac{T}{2} \mid T3 = \frac{T}{4}$$

$$J1 = \frac{(11 \cdot \Delta a - 8 \cdot \Sigma a) \cdot T^2 + (16 \cdot \Delta v - 48 \cdot \Sigma v) \cdot T + 96 \cdot \Delta s}{3 \cdot T^3}$$

$$J2 = -\frac{5 \cdot \Delta a \cdot T^2 - 48 \cdot \Sigma v \cdot T + 96 \cdot \Delta s}{3 \cdot T^3}$$

$$J3 = \frac{(11 \cdot \Delta a + 8 \cdot \Sigma a) \cdot T^2 + (-16 \cdot \Delta v - 48 \cdot \Sigma v) \cdot T + 96 \cdot \Delta s}{3 \cdot T^3}$$

Candidate 3X: Three Piece Other

Examine any other candidates based on other fixed time allotments found from Eq. 3. Then solve as for candidate 3F above.

Candidate Selection

If candidates for all moves in an application specified path can be calculated a priori then select the set of candidates that minimize worst case discontinuity in jerk by examining the values of Jn for each potential cubic piece in the overall spline. If using a higher order polynomial, minimize discontinuity at piece boundaries in the highest order polynomial coefficient. Otherwise, find the maximum magnitude jerk for each candidate, and select candidates to minimize that quantity.

Calculation of Other Parameters

Each cubic in the above-mentioned candidates are defined by the Jn and Tn of the pieces because:

The disclosure has been described with reference to various specific embodiments and techniques. However, it should be understood that many variations and modifications are possible while remaining within the scope of the disclosure.

What is claimed is:

1. A method for scanning a light beam spot spatially over one or more biosensors supported by a microplate with an optical scanner system having:
    at least one adjustable optic to deflect the light beam spot to an x and y position on the microplate;
    a set of properties that describe the x and y position on the microplate of the beam spot at any time;
    a series of points in time and at each point in time a value for each of the properties and the $1^{st}$ through the $(n-1)^{th}$ order rates of change of each of the properties;
    the method comprising:
    defining an axis for each property used to describe the state of the beam spot;
    calculating for each axis an $n^{th}$ order piecewise polynomial function of time between each point in the series of points in time that equals the specified axis value and the $1^{st}$ through the $(n-1)^{th}$ order rates of change where the piecewise polynomial function of time is substantially continuous throughout in axis value and the $1^{st}$ through the $(n-1)^{th}$ order rates of change;
    producing a series of elapsed times between each point in the series of points in time;
    calculating each axis value from the polynomial function at each point in the series of elapsed times;
    calculating the x and y locations of the scan path from the axis values at each point in time; and
    sending the calculated x and y locations to the optical scanner system when each point in elapsed time series occurs to cause the optical scanner system to deflect the light beam and scan the beam spot over the defined scan path.

2. The method of claim 1, wherein additional points in time, together with the state of the beam spot at each additional point in time together with the $1^{st}$ through the $(n-1)^{h}$ order rates of change of the state of the beam spot are appended to a scan path that is in progress.

3. The method of claim 1, wherein the piecewise polynomial function is a cubic spline.

4. The method of claim 1, wherein the piecewise polynomial function is of the $3^{rd}$ order and has 3-pieces.

5. The method of claim 1, wherein in between at least one pair of consecutive points in time:
    there are n polynomial pieces, and the duration of each of the polynomial pieces are fixed ratios of the total duration between the points in time;
    there are n polynomial pieces, where the highest order coefficient of the n polynomial pieces have substantially the same absolute value, and the duration of each polynomial piece is a calculated parameter; or

| $s1_0 = s_1$ | $v1_0 = v_1$ | $a1_0 = a_1$ |
|---|---|---|
| $s2_0 = s1(T1)$ | $v2_0 = v1(T1)$ | $a2_0 = a1(T1)$ |
| $s2_0 = s1 + v1_0 \cdot T1 + \frac{1}{2}a1_0 \cdot T1^2 + \frac{1}{6}J1 \cdot T1^3$ | $v2_0 = v1_0 + a1_0 \cdot T1 + \frac{1}{2}J1 \cdot T1^2$ | $a2_0 = a1_0 + J1 \cdot T1$ |
| $s3_0 = s2(T2)$ | $v3_0 = v2(T2)$ | $a3_0 = a2(T2)$ |
| $s3_0 = s2_0 + v2_0 \cdot T1 + \frac{1}{2}a2_0 \cdot T1^2 + \frac{1}{6}J2 \cdot T1^3$ | $v3_0 = v2_0 + a2_0 \cdot T1 + \frac{1}{2}J2 \cdot T1^2$ | $a3_0 = a2_0 + J2 \cdot T1$ | the polynomial is of the $3^{rd}$ order, there are two polynomial pieces, and the $3^{rd}$ order coefficient and duration of each piece are calculated parameters.

6. The method of claim 1, wherein the polynomial in between each pair of consecutive points in time is calculated using a method that minimizes the maximum discontinuity in the $n^{th}$ order rate of change for a section of the scan path.

7. The method of claim 6, wherein the section of the scan path includes the entire scan path.

8. The method of claim 1, wherein the defined axes are combined to form x and y positions.

9. The method of claim 1, wherein the elapsed times are representative of elapsed time in the real time, the elapsed times have intervals that are substantially smaller than the smallest interval of the specified selected time series, and the properties include at least one of: x position, y position, oscillation amplitude, oscillation direction, oscillation frequency, oscillation phase, and combinations thereof.

10. A system for scanning a light beam spot over one or more biosensors supported by a microplate with an optical scanner system, comprising:
a motion controller configured to:
receive a series of points in time, and at each point in time the value of each scan path property and the $1^{st}$ through the $(n-1)^{th}$ order rate of change of each of the properties;
calculate a series of elapsed points in time between each received point in time;
calculate the x and y locations of the scan path at each point of elapsed points in time as defined in claim 1; and
an optical scanner system configured to receive the x and y locations of the scan path at each elapsed point in time, and thereafter deflect the light beam to scan the beam spot over the scan path.

11. The system of claim 10, wherein the elapsed times are representative of elapsed time in real time, the elapsed times have intervals that are substantially smaller than the smallest interval of the series of points in time, and the properties include at least one of: x position, y position, oscillation amplitude, oscillation direction, oscillation frequency, oscillation phase, and combinations thereof.

12. The system of claim 10, further comprising first and second digital amplifiers operably connected to the controller and respectively configured to convert the x and y locations of the scan path to drive output positions x and y, and to amplify the drive output positions x and y.

13. The system of claim 12, wherein the amplified output positions x and y comprise respective x and y currents or voltages.

14. The system of claim 10, wherein the optical scanner system includes one of: a scanning galvanometer, a flexure-based scanning mirror, a micro-electro-mechanical system (MEMs) mirror, an oscillating plane mirror, a rotating multi-faceted minor, and a piezo-electric-driven mirror.

15. The system of claim 10, further comprising a system controller operably connected to the motion controller and configured to input the series of points in time, and at each point in time the value of each scan path property and the $1^{st}$ through the $(n-1)^{th}$ order rate of change of each of the properties to the multi-axis controller.

* * * * *